(12) United States Patent
Kita et al.

(10) Patent No.: US 7,598,010 B2
(45) Date of Patent: Oct. 6, 2009

(54) TRIARYLAMINE DIMER DERIVATIVE HAVING AMORPHOUS PHASE

(75) Inventors: Yoshio Kita, Neyagawa (JP); Yasuhiro Yamasaki, Neyagawa (JP)

(73) Assignee: Orient Chemical Industries, Ltd., Osaka (JP)

( * ) Notice: Subject to any disclaimer, the term of this patent is extended or adjusted under 35 U.S.C. 154(b) by 608 days.

(21) Appl. No.: 10/998,913

(22) Filed: Nov. 30, 2004

(65) Prior Publication Data

US 2005/0154234 A1 Jul. 14, 2005

(30) Foreign Application Priority Data

Dec. 3, 2003 (JP) ............................. 2003-404134
Dec. 19, 2003 (JP) ............................. 2003-422151

(51) Int. Cl.
G03G 15/02 (2006.01)
C07C 211/00 (2006.01)

(52) U.S. Cl. ..................... 430/58.85; 564/307; 564/434

(58) Field of Classification Search ................. 564/307, 564/434; 430/58.85

See application file for complete search history.

(56) References Cited

U.S. PATENT DOCUMENTS

| 5,476,968 | A | * | 12/1995 | Imai et al. ................... 564/309 |
| 6,228,547 | B1 | * | 5/2001 | Kobayashi et al. ............. 430/72 |
| 6,242,115 | B1 | * | 6/2001 | Thomson et al. ............. 428/690 |
| 6,242,648 | B1 | | 6/2001 | Yamasaki et al. ........... 564/405 |
| 2003/0064308 | A1 | | 4/2003 | Kita et al. .................. 430/58.8 |

FOREIGN PATENT DOCUMENTS

| EP | 1296192 | 3/2003 |
| EP | 1300390 | 4/2003 |
| JP | 08-291115 | 11/1996 |
| JP | 8291115 | 11/1996 |
| JP | 09-316038 | 12/1997 |
| JP | 2000-256276 | 9/2000 |
| JP | 2001-335542 | 12/2001 |
| JP | 2003-021921 | 1/2003 |
| JP | 2003-089681 | 3/2003 |
| JP | 2003-146950 | 5/2003 |

OTHER PUBLICATIONS

Forsythe et al., Journal of Physical Chemistry, vol. 104, No. 16, pp. 3948-3952 (2000).*
Okumoto, K. et al. "Development of new hole-transporting amorphous molecular materials for organic electroluminescent devices and their charge-transport properties" Materials Science and Engineering B, Elsevier Sequoia, Lausanne, Switzerland, vol. 85, No. 2-3, Aug. 22, 2001, pp. 135-139, XP004255448, ISSN: 0921-5107.
Database WPI, Section Ch, Week 199703 Derwent Publications Ltd., London, UK; AN 1997-029486 XP002347997 & JP 08 291115 A (Bandon Chem Ind Ltd) Nov. 5, 1996, Abstract.

* cited by examiner

Primary Examiner—Porfirio Nazario Gonzalez
(74) Attorney, Agent, or Firm—Steptoe & Johnson LLP

(57) ABSTRACT

A triarylamine dimer derivative is represented by the following chemical formula [1]

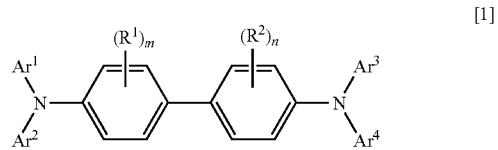

(in the chemical formula [1]: —$Ar^1$, —$Ar^2$, —$Ar^3$ and —$Ar^4$ are aryl groups being to have a substitutional group respectively, —$R^1$ and —$R^2$ are same or different to each other and one thereof is selected from the group consisting of a hydrogen atom, an alkyl group, an alkoxyl group and a halogen atom; m and n are from 0 to 4; and with a proviso that —$Ar^1$ and —$Ar^2$, —$Ar^3$ and —$Ar^4$ are being to bind respectively to compose a cyclic structure group having a nitrogen atom) having an amorphous phase indicated by spectrum of powder X-ray diffractometry. The triarylamine dimer derivative is used for a charge transport material, an electrophotographic photosensitive conductor having thereof, an electroluminescence elemental device having a hole transport material thereof.

6 Claims, 14 Drawing Sheets

TRIARYLAMINE DIMER DERIVATIVE HAVING AMORPHOUS PHASE

BACKGROUND OF THE INVENTION

This invention relates to a useful triarylamine dimer derivative having amorphous phase (non-crystal phase) for a charge transport material of an electrophotographic photosensitive conductor and a hole transport material of an electroluminescence elemental device, its manufacturing method, and organic semiconductors that applies them.

With regard to the organic electrophotographic photosensitive conductor, the organic semiconductor such as the layer-built electrophotographic photosensitive conductor is widely used.

The layer-built electrophotographic photosensitive conductor is laminated with a charge generation layer including a charge generation material such as phthalocyanine-type compound that generates the charge by irradiation of light and a charge transport layer including a charge transport material that transports the charge to a surface of the conductor.

Various solid solutions, that the charge transport material is dissolved into a binder polymer, are used for the charge transport layer of the organic semiconductor.

It is necessary that the charge transport layer is formed to be uniform. If the charge transport material precipitates to be hardly uniform on the occasion of forming thereof, it causes white hole fogginess on the occasion of printing. Therefore it is desired that the charge transport material has sufficient solubility into a binder polymer solution.

The charge transport materials used for the organic electrophotographic photosensitive conductor are instanced with a triarylamine derivative, an oxazole derivative, an oxadiazole derivative, a pyrazoline derivative, a hydrazone derivative, a hydrazine derivative, a triazine derivative, a quinazoline derivative, a styryl-type derivative, a styryltriphenylamine derivative, a butadiene derivative, a carbazole derivative and a benzofuran derivative, etc.

Above all, the triarylamine dimer derivative has an excellent charge transport property, and is widely used for the charge transport material of the organic electrophotographic photosensitive conductor of a printer or a copy machine, and the hole transport material of the organic electroluminescence elemental device.

The usual triarylamine dimer derivatives are instanced with N,N'-diphenyl-N,N'-bis(1-naphthyl)-4,4'-diaminobiphenyl (alpha-NPD) represented by the following chemical formula [A],

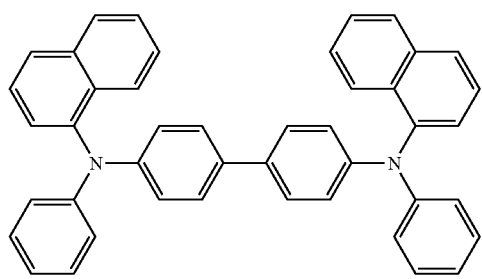

[A]

N,N'-diphenyl-N,N'-ditolyl-4,4'-diaminobiphenyl (TPD) represented by the following chemical formula [B].

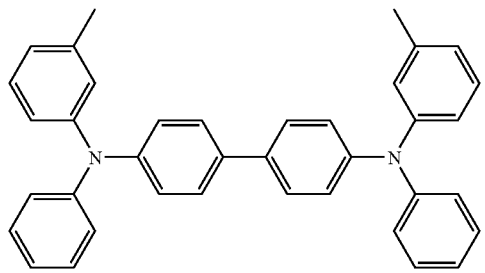

[B]

Particularly alpha-NPD is widely used for the hole transport material in a field of the organic electroluminescence. And it is known that alpha-NPD has the excellent charge transport property. It is difficult to form the layer thereof because of its very low solubility into a solvent or a resin. A vacuum deposition method and so on is indispensable. Therefore, alpha-NPD as the charge transport material is not put into a practical use in a field of the electrophotographic photosensitive conductor that is formed by applying of the layer as a general procedure.

On the other hand, it is known that TPD is used for the charge transport material of the electrophotographic photosensitive conductor. However TPD often causes problems of the insufficient solubility or the crystallization on the occasion of forming the layer as the sensitive conductor onto a drum.

Up to now for example, patents about the following improved triarylamine derivatives have been applied.

In Japanese Patent Provisional Publication No. 2003-21921, examples of N,N'-diphenyl-N,N'-bis(2-naphthyl)-4,4'-diaminobiphenyl (beta-NPD) derivative for the charge transport material in the field of the electrophotographic photosensitive conductor are described. An alkyl substitutional group especially the methyl group is introduced to the derivative in order to improve the solubility.

In Japanese Patent Provisional Publication No. 2003-89681, triphenylamine dimer (3,4-TPD) derivative represented by the following chemical formula [C]

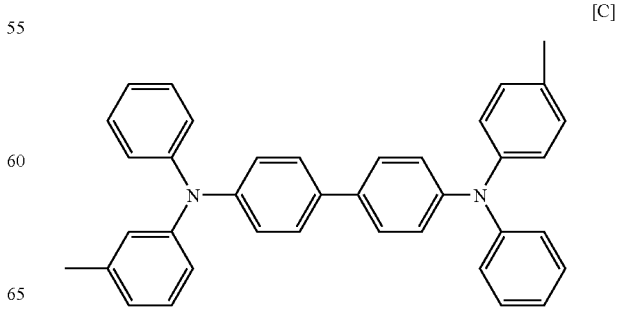

[C]

is described. The derivative has its excellent electronic property because of having very little content of impurity (TPD analog). And the derivative has an excellent formation property of the layer because of a low crystallization property.

In Japanese Patent Provisional Publication No. 8-291115, a triphenylamine derivative represented by the following chemical formula [D]

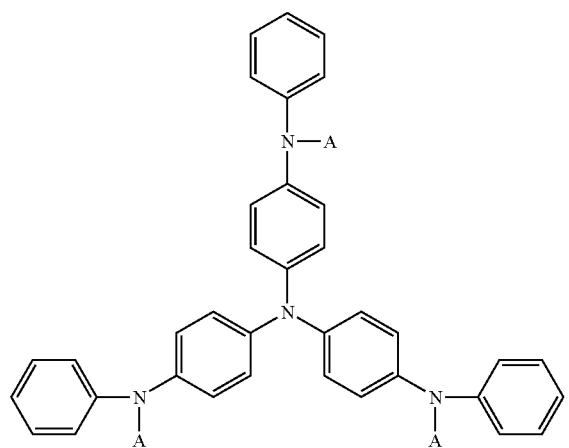

(in the chemical formula [D], -A is 1-naphthyl group or 2-naphthyl group) is described. The derivative can form a thin layer without using a binder resin by itself because of keeping amorphous state, namely glass state at normal temperature. And the derivative is useful for amorphous electronic materials having heat resistance because of having glass transition point of 100 degrees Centigrade.

In Japanese Patent Provisional Publication No. 2001-335542, the derivative represented by the following chemical formula [E]

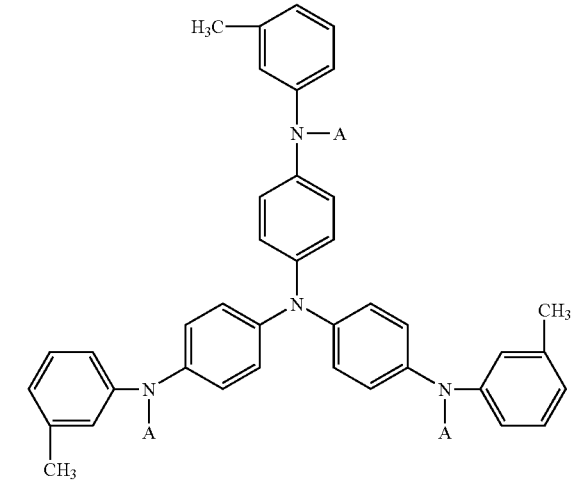

(in the chemical formula [E], -A is 1-naphthyl group or 2-naphthyl group), that the above-mentioned triphenylamine derivative (the chemical formula [D]) is substituted by methyl groups, is described. The derivative (the chemical formula [E]) is used for the hole transport material of the organic electroluminescence elemental device.

In Japanese Patent Provisional Publication No. 9-316038, a diamine derivative represented by the following chemical formula [F]

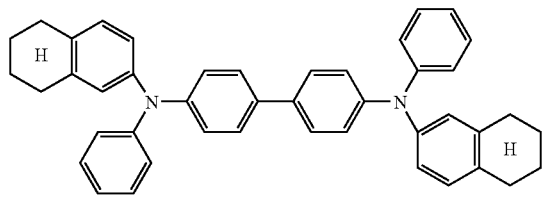

is described. The derivative is useful to the hole transport material used for the organic electroluminescence elemental device or the electrophotographic photosensitive conductor.

In Japanese Patent Provisional Publication No. 2003-146950, the bisphenyl cycrohexane derivative represented by the following chemical formula [G]

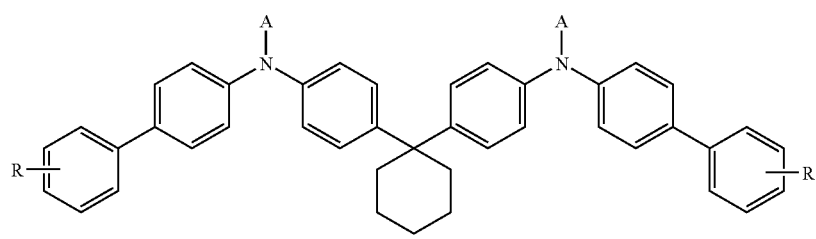

(in the chemical formula [G], -A is a substituted or a non-substituted aromatic hydrocarbon group, etc., —R is a hydrogen atom or an alkyl group, etc.) is described. The derivative has excellent heat resistance on the occasion of a vapor deposition process, high glass transition point, electronic stability and chemical stability.

In Japanese Patent Provisional Publication No. 2000-256276, a method of manufacturing the triarylamine dimer by Ullmann reaction, that polyethylene glycol or dialkyl ether or monoalkyl ether as a reaction accelerator is used instead of crown ether (for example, 18-crown-6), is described.

Moreover, in Japanese Patent Provisional Publication No. 2003-89681, the similar method of manufacturing the triarylamine dimer is described.

Particularly it is necessary that the charge transport layer of the electrophotographic photosensitive conductor is formed to be uniform. Generally, the prior improved triarylamine dimer derivatives are prepared by a purification procedure such as recrystallization to have the crystal phase. These derivatives cause still the insufficient solubility into the organic solvent, or the crystallization on the occasion of forming the layer as the sensitive conductor onto the drum. Therefore these derivatives cause the problem that the charge transport layer becomes hardly uniform.

Moreover when an aliphatic substitutional group is introduced to the triarylamine dimer derivative for increasing of the solubility into the organic solvent, the aliphatic substitutional group having a long alkyl group makes the charge transport property of the triarylamine dimer derivative decrease. And the triarylamine dimer derivative cannot acquire the sufficient properties on the occasion of using for the charge transport layer of the electrophotographic photosensitive conductor.

SUMMARY OF THE INVENTION

It is an object of the present invention to provide a triarylamine dimer derivative without a introduced long substitutional aliphatic group, that has sufficient solubility into the organic solvent, excellent sensitivity and amorphous phase, and forms a thin charge transport layer by a simple coating method such as a dipping method or a spin-coating method, and a manufacturing method thereof.

It is another object of the present invention to provide a organic semiconductor using the triarylamine dimer derivative such as a charge transport material that does not crystallize on the occasion of forming of the charge transport layer, an electrophotographic photosensitive conductor or a hole transport material having the charge transport material, an electroluminescence elemental device made from the charge transport material as the hole transport material.

For accomplishing the foregoing object, the inventors made earnest efforts of applying the triarylamine dimer derivative to the organic semiconductor of the electrophotographic photosensitive conductor, etc.

It is found that a specific triarylamine dimer derivative having amorphous phase as crystal transformation has very sufficient solubility, excellent solute stability, an excellent formation property of the layer on the occasion of using for a charge transport material of a photosensitive conductor, an excellent photosensitive property such as dark decrement. Further it is found that the triarylamine dimer derivative is used for the organic semiconductor such as the electrophotographic photosensitive conductor, the hole transport material, the organic electroluminescence elemental device.

A triarylamine dimer derivative of the present invention developed for accomplishing the foregoing object under the knowledge is represented by the following chemical formula [1]

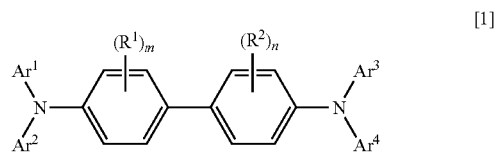

(in the chemical formula [1]:
—$Ar^1$, —$Ar^2$, —$Ar^3$ and —$Ar^4$ are aryl groups being to have a substitutional group respectively, —$R^1$ and —$R^2$ are same or different to each other and one thereof is selected from the group consisting of a hydrogen atom, an alkyl group, an alkoxyl group and a halogen atom, m and n are from 0 to 4;
and with a proviso that —$Ar^1$ and —$Ar^2$, —$Ar^3$ and —$Ar^4$ are being to bind respectively to compose a cyclic structure group having a nitrogen atom)

having an amorphous phase indicated by spectrum of powder X-ray diffractometry.

Examples of the cyclic structure group having the nitrogen atom that —$Ar^1$ and —$Ar^2$, —$Ar^3$ and —$Ar^4$ are bound respectively are a carbazole group, an iminodibenzyl group, and an iminostilbene group.

—$Ar^1$, —$Ar^2$, —$Ar^3$ and —$Ar^4$ of the triarylamine dimer derivative of the present invention may be aryl groups which are at least one selected from the group consisting of a phenyl group, an alpha-naphthyl group, a beta-naphthyl group, a biphenyl group, a terphenyl group, an anthranyl group, a phenanthryl group and an acenaphthyl group being to have a substitutional group. Examples of the substitutional group, that the above-mentioned aryl groups of —$Ar^1$, —$Ar^2$, —$Ar^3$ and —$Ar^4$ are to have, are a hydrogen atom, an alkyl group, an alkoxyl group, an alkenyl group, an alkynyl group, a dialkylamino group, an imino group and a halogen atom.

Above all, the usual and preferable aryl group of —$Ar^1$, —$Ar^2$, —$Ar^3$ and —$Ar^4$ is the phenyl group being to have the substitutional group or the naphthyl group being to have the substitutional group.

Concretely, the triarylamine dimer derivative is represented by the following formula [3]

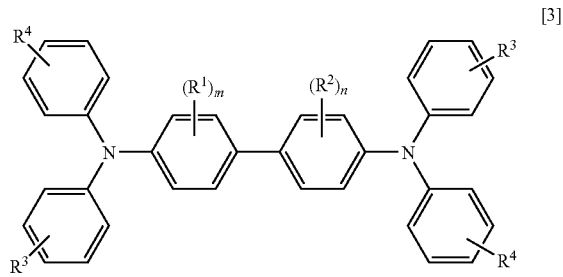

whose —$Ar^1$, —$Ar^2$, —$Ar^3$ and —$Ar^4$ are the phenyl group being to have the substitutional group.

Moreover the triarylamine dimer derivative is represented by the following formula [4]

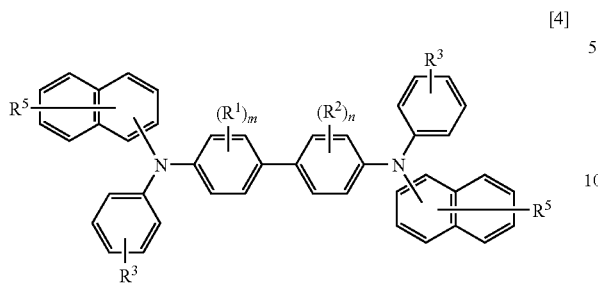

[4]

whose —Ar$^1$ and —Ar$^4$ are the naphthyl group (such as 1-naphthyl and 2-naphthyl) being to have the substitutional group and —Ar$^2$ and —Ar$^3$ are the phenyl group being to have the substitutional group.

Examples of —R$^1$ and —R$^2$ in the chemical formulae [1], [3] or [4] are a hydrogen atom; an alkyl group having 1 to 4 carbons such as methyl group, ethyl group, propyl group, isopropyl group, butyl group and tert-butyl group; an alkoxyl group having 1 to 4 carbons such as methoxyl group, ethoxyl group and isopropoxyl group; a halogen atom such as chlorine atom, bromine atom and fluorine atom.

Examples of —R$^3$, —R$^4$ and —R$^5$ in the chemical formulae [3] or [4] are a hydrogen atom; an alkyl group having 1 to 4 carbons such as methyl group, ethyl group, propyl group, isopropyl group, butyl group and tert-butyl group; an alkoxyl group having 1 to 4 carbons such as methoxyl group, ethoxyl group and isopropoxyl group; an alkenyl group such as vinyl group, propenyl group and butenyl group; an alkynyl group such as —C≡CH and —C≡CCH$_3$; a dialkylamino group such as dimethylamino group and diethylamino group; an imino group; a halogen atom such as chlorine atom, bromine atom and fluorine atom.

Although the following triarylamine dimer derivatives are mentioned furthermore concretely, it is not to be construed to limit them.

Compound Example 1

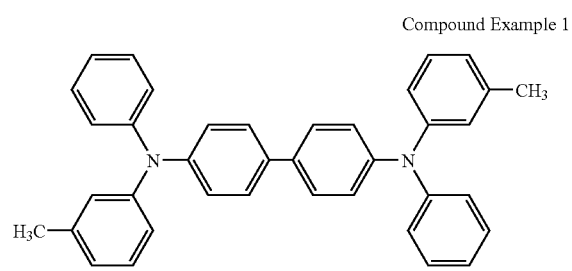

Compound Example 2

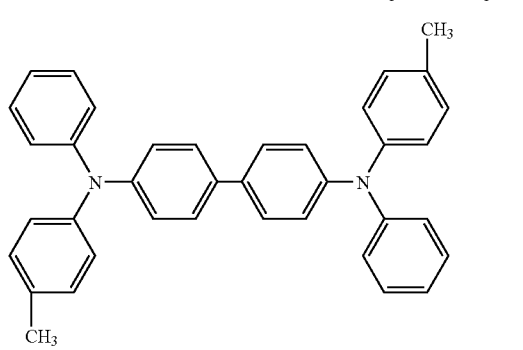

Compound Example 3

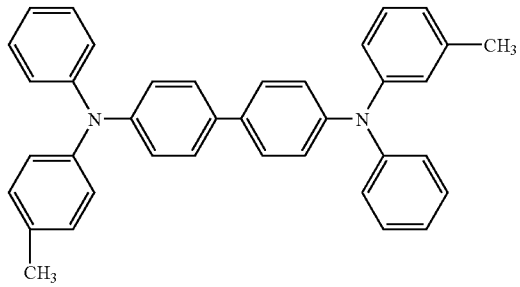

Compound Example 4

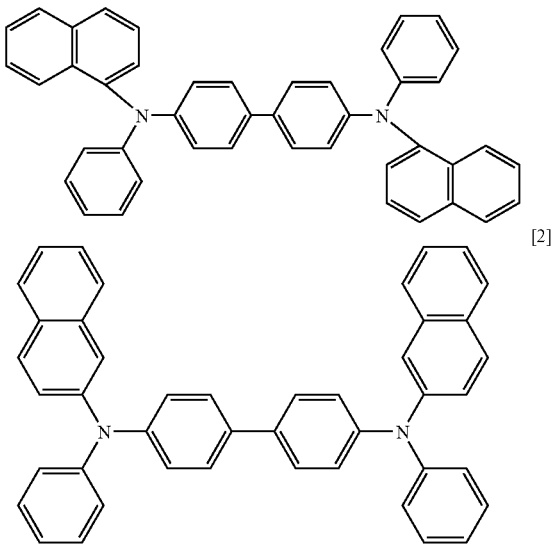

Compound Example 5

Above all, N,N'-diphenyl-N,N'-bis(2-naphthyl)-4,4'-diaminobiphenyl of the Compound Example 5 represented by the above-mentioned chemical formula [2] is preferable especially.

A manufacturing method of the amorphous triarylamine dimer derivative of the present invention contains steps of:
heating and fusing steps of a solid of the triarylamine dimer derivative represented by the above-mentioned chemical formula [1] being to have a crystal phase,
then quenching and solidifying steps thereof.

It is preferable that the heating and fusing steps are executed under reduced pressure or nitrogen atmosphere for preventing thermal decomposition thereof.

In the manufacturing method of an amorphous triarylamine dimer derivative of the present invention, the quenching step is executed from a fusing temperature thereof to glass transition point or below it preferably.

Another manufacturing method of the amorphous triarylamine dimer derivative of the present invention may contain steps of:
a dissolving step of a solid of the triarylamine dimer derivative represented by the above-mentioned chemical formula [1] being to have a crystal phase, into an organic solvent,
then a re-precipitating step by addition of a poor solubility solvent.

It is preferable that the organic solvent is selected from the group consisting of xylene, dichloromethane, chloroform, tetrahydrofuran, dimethyl formamide and ethyl acetate. And it is preferable that the poor solubility solvent is an alcohol solvent which is selected from the group consisting of methanol, ethanol, isopropanol and butanol.

The organic solvent and the poor solubility solvent are not to be construed to limit the above-mentioned solvents. The organic solvent may be the other solvent that can dissolve the solid of the triarylamine dimer derivative efficiently. The poor solubility solvent may be the other solvent that can re-precipitate the triarylamine dimer derivative efficiently.

It is preferable that the triarylamine dimer derivative having the amorphous phase is manufactured by the above-mentioned manufacturing method thereof.

A charge transport material of the present invention uses the above-mentioned triarylamine dimer derivative having the amorphous phase.

An electrophotographic photosensitive conductor of the present invention has the charge transport material that includes the above-mentioned triarylamine dimer derivative having the amorphous phase.

The charge transport material may be used for the monolayer electrophotographic photosensitive conductor or the layer-built electrophotographic photosensitive conductor that the photosensitive layer is made of the separated charge generation layer and charge transport layer.

A hole transport material of the present invention has the charge transport material that includes the above-mentioned triarylamine dimer derivative having the amorphous phase.

An electroluminescence elemental device of the present invention is constructed with the hole transport material having the charge transport material that includes the above-mentioned triarylamine dimer derivative having the amorphous phase.

As explained above, the triarylamine dimer derivative having the amorphous phase has the more excellent solubility than the derivative having the crystal phase into the organic solvent such as tetrahydrofuran (THF), dimethyl formamide (DMF), xylene, chloroform, dichloromethane. Above all, N,N'-diphenyl-N,N'-bis(2-naphthyl)-4,4'-diaminobiphenyl has the further more excellent solubility and solute stability than alpha-NPD as structural isomer thereof and TPD as the usual charge transport material.

Therefore the triarylamine dimer derivative having the amorphous phase is the optimum for forming the thin layer of the charge transport material of the electrophotographic photosensitive conductor or the electroluminescence elemental device because of having the advantageous solubility. The charge transport layer of the organic photosensitive conductor is formed by the simple applying method such as the dipping method and the spin-coating method using the triarylamine dimer derivative having the amorphous phase on the occasion of manufacturing the electrophotographic photosensitive conductor.

When the triarylamine dimer derivative having the amorphous phase is used for the charge transport layer, the moderate or excellent photosensitive conductor that has the excellent electrification property, the excellent sensitive resistance, the excellent electric potential resistance, and the excellent photosensitive property such as dark decrement, is prepared.

Moreover when the triarylamine dimer derivative having the amorphous phase is used for the hole transport material of the electroluminescence elemental device, the stable thin layer that dose not crystallize is formed.

DETAILED DESCRIPTION OF THE INVENTION

Figure 1:
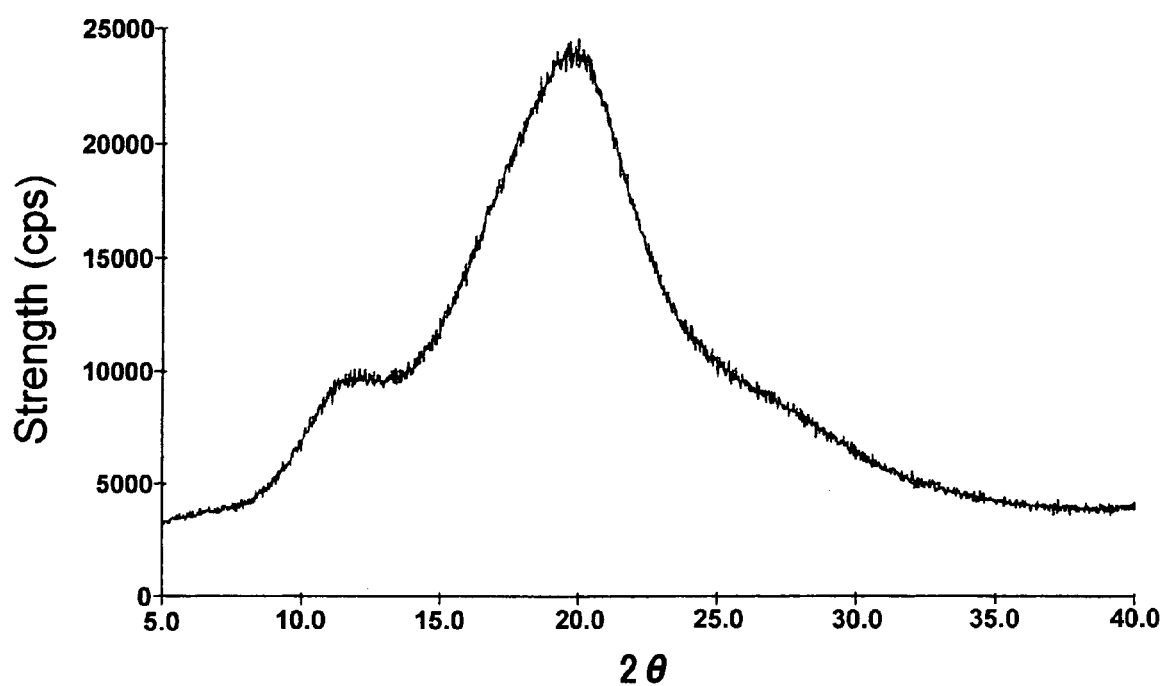
FIG. 1 is a powder X-ray diffractometry spectrum of 3,3-TPD having the amorphous phase prepared in Example 1.

In the present invention, the triarylamine dimer derivative is prepared to be amorphous by the quenching procedure or the re-precipitating procedure.

It is confirmatory that the prepared triarylamine dimer derivative has the amorphous phase by indicating no obvious peaks of powder X-ray diffractometry.

It is confirmatory that the derivative having the amorphous phase and the derivative having crystal phase have the same chemical structure by measurements of infrared spectroscopy (IR), $^1$H-nuclear magnetic resonance ($^1$H-NMR), $^{13}$C-nuclear magnetic resonance ($^{13}$C-NMR), elemental analysis and high-speed liquid chromatography (HPLC).

The triarylamine dimer derivative having the crystal phase as the starting material may be commercially available, or synthetically available by any known method. The triarylamine dimer derivative may be used solely or plurally as mixture thereof.

The organic electrophotographic photosensitive conductor of the present invention is for example the function-separate photosensitive conductor having the thin layer that is formed by layer-building each of the charge generation layer and the charge transport layer onto a conductive support.

It is preferable that the organic electrophotographic photosensitive conductor is applied to the function-separate photosensitive conductor having construction of the two layers because the electronic property and the photosensitive property by the crystal transformation of the charge generation material are demonstrated effectively. In the function-separate photosensitive conductor having construction of the two layers, the generated charge is hardly trapped, the layers do not impede the function each other, and the charge is transported to the surface of the photosensitive conductor effectively.

As the charge generation materials, titanyl phthalocyanine, mu-oxo-aluminum phthalocyanine dimer or mu-oxo-gallium phthalocyanine dimer, etc. is used.

As substrate of the conductive support, metal of aluminum or nickel, or film deposited by metal is used. The substrates are prepared to be a drum shape, a sheet shape, or a belt shape.

For example, the organic electrophotographic photosensitive conductor is prepared as follows.

The charge generation material onto the conductive support forms the thin charge generation layer, to begin with. The thin charge generation layer is formed by deposition of the charge generation material onto the conductive support. Moreover the charge generation layer is formed by preparing of a coating solution that the charge generation material is dispersed into a solution of a solvent and a dissolved binding resin, and coating thereof onto the support usually.

For a procedure of dispersing of the charge generation material, a ball mill, a sand mill or a paint shaker is used.

For a procedure of coating for the charge generation layer, for example a bar coater, a dip coater, a spin coater or a roller coater is used suitably. It is not to be construed to limit them. Continuously, the coated charge generation layer may be dried at 30 to 200 degrees Centigrade for 5 minutes to 2 hours under standing or ventilating.

The solvent for this coating solution for the charge generation layer can disperse homogeneously the charge generation material without dissolving thereof, and can dissolve the used binding resin if necessary. And it is not to be construed to limit. Examples of the solvent are an alcohol solvent such as methanol, ethanol, isopropanol, butanol; an aromatic solvent such as toluene, xylene, tetralin; a halogenated solvent such as dichloromethane, chloroform, trichloroethylene, carbon tetrachloride; an ester solvent such as ethyl acetate, propyl acetate; an ether solvent such as ethylene glycol monoethyl ether, dioxane, tetrahydrofuran; dimethyl formamide; dimethyl sulfoxide.

The binding resin may be selected from extensive insulating resins. Examples of preferable resin are a condensation resin such as polycarbonate, polyester, polyamide, polyarylate; an addition polymer such as polystyrene, polyacrylate, styrene-acryl copolymer, polyacrylamide, polymethacrylate, poly(vinyl butyral), poly(vinyl alcohol), polyacrylonitrile, polyacryl-butadiene copolymer, poly(vinyl chloride), vinyl chloride-vinyl acetate copolymer; an organic photoconductivity resin such as poly-N-vinylcarbazole, poly(vinyl anthracene); polysulfone, polyether sulfone; silicone resin; epoxy resin; urethane resin. Some of them may be used to mix suitably.

It is preferable that a ratio by weight of the amount of the used binding resin to the charge generation material is 0.1 to 3. If the ratio by the weight is more than 3, concentration of the charge generation material in the charge generation layer is dilute and the photosensitivity thereof decreases. It is preferable that the thickness of the charge generation layer is 0.05 to 5.0 microns. The thickness is 10 microns or less usually.

Then the thin charge transport layer including the triarylamine dimer derivative as the charge transport material is coated onto the charge generation layer. A procedure of coating for the charge transport layer is the similar procedure of coating for the charge generation layer. Namely the charge transport material is dissolved into the solvent with the binding resin if necessary, coated onto the charge generation layer uniformly, and then dried.

The solvent for this coating solution for the charge transport layer can dissolve the triarylamine dimer derivative effectively, and can dissolve the binding resin used if necessary. And it is not to be construed to limit. Examples of the solvent are an aromatic solvent such as toluene, xylene, tetralin; a halogenated solvent such as dichloromethane, chloroform, trichloroethylene, carbon tetrachloride; an ester solvent such as ethyl acetate, propyl acetate; an ether solvent such as ethylene glycol monoethyl ether, dioxane, tetrahydrofuran; dimethyl formamide; dimethyl sulfoxide.

The binding resin for forming the charge transport layer may be used as the similar binding resin used for the above charge generation layer. It is preferable that a ratio by weight of the amount of the used binding resin to the charge transport material is 0.1 to 5. If the ratio by the weight is more than 5, the concentration of the charge transport material in the charge transport layer is dilute and the photosensitivity thereof decreases. It is preferable that the thickness of the charge transport layer is 5 to 50 microns. The thickness is 100 microns or less usually.

The electrophotographic photosensitive conductor may be additionally coated with a protecting layer of its surface.

Incidentally, the charge generation layer, the charge transport layer or the protecting layer of the surface may include with various additive agents such as a known sensitizer; a degradation inhibitor illustrated by a an antioxidant of amines or phenols, an ultraviolet absorption agent of benzophenones.

Hereafter, the invention is explained by synthetic examples and examples concretely. This invention is not limited to them.

Synthetic Example 1

N,N'-diphenyl-N,N'-bis(3-tolyl)-4,4'-diaminobiphenyl (3,3-TPD) was synthesized as follows.

1.0 g (2.46 mmol) of 4,4'-diiodobiphenyl and 20 ml of o-dichlorobenzene were added to a 100 ml four-necked flask made of glass. Furthermore 1.08 g (5.90 mmol) of m-methyldiphenylamine, 0.104 g of poly(ethylene glycol) PEG-6000 as a reaction accelerator that was available from Wako Pure Chemical Industries, Ltd., 2.73 g (0.0198 mol) of potassium carbonate and 0.635 g (9.87 mmol) of powdered copper were added thereto. It was determined for tracing by the high-speed liquid chromatography. And it was stirred and refluxed for 22 hours until no peaks of starting materials and intermediates were determined. It was filtrated at the hot temperature. The product was washed with dichloromethane until color of the filtrate was to be light. The solvent was distilled under reduced pressure. Residual product was purified by silica gel column chromatography to obtain 3,3-TPD that is represented by Compound Example 1.

Synthetic Example 2

N,N'-diphenyl-N,N'-bis(4-tolyl)-4,4'-diaminobiphenyl (4,4-TPD) was synthesized as follows.

1.0 g (2.46 mmol) of 4,4'-diiodobiphenyl and 20 ml of o-dichlorobenzene were added to a 100 ml four-necked flask made of glass. Furthermore 1.08 g (5.90 mmol) of 4-methyidiphenylamine, 0.104 g of poly(ethylene glycol) PEG-6000 as the reaction accelerator that was available from Wako Pure Chemical Industries, Ltd., 2.73 g (0.0198 mol) of potassium carbonate and 0.635 g (9.87 mmol) of powdered copper were added thereto. It was determined for tracing by the high-speed liquid chromatography. And it was stirred and refluxed for 22 hours until no peaks of starting materials and intermediates were determined. It was filtrated at the hot temperature. The product was washed with dichloromethane until color of the filtrate was to be light. The solvent was distilled under reduced pressure. Residual product was purified by silica gel column chromatography to obtain 1.01 g of 4,4-TPD that is represented by Compound Example 2 at 78.7% yield.

Synthetic Example 3

The mixture of 3,3-TPD, 4,4-TPD and N,N'-diphenyl-N-(3-tolyl)-N'-(4-tolyl)-4,4'-diaminobiphenyl (3,4-TPD) that is represented by Compound Example 3 was synthesized as follows.

Mixture of 438 g (2.43 mol) of 3-methyldiphenylamine and 49 g (0.27 mol) of 4-methyidiphenylamine whose mol ratio is 90:10 were added to a 5000 ml four-necked flask made of glass. Further 28 g (4.4 mol) of powdered copper was added thereto. It was heated at 30 degrees Centigrade. 450 g (1.1 mol) of 4,4'-diiodobiphenyl and 47 g of poly(ethylene glycol) PEG-6000 that was available from Wako Pure Chemical Industries, Ltd. were added thereto. It was heated at 100 degrees Centigrade, and then 307 g (2.2 mol) of powdered potassium carbonate was added thereto. It was heated at 205 degrees Centigrade, and stirred for 14 hours. After cooling, DMF was added thereto, and stirred at 130 degrees Centigrade for 1 hour. After cooling till 90 degrees Centigrade, hot water was added thereto. It was stirred for 2 hours. After filtration, filtrated cake was washed with hot water to obtain brown solid. The obtained brown solid was dispersed and stirred into DMF for 1 hour, filtrated and washed with DMF and methanol. The obtained solid was refluxed with activated carbon in xylene for 1 hour. After cooling till 70 degrees Centigrade, it was filtrated. The filtrate was passed through a column packing adsorbent to obtain colorless solution. The solvent was distilled under reduced pressure. Precipitated crystals were filtrated out and dried to obtain 455 g of mixture of TPD.

Synthetic Example 4

N,N'-diphenyl-bis(1-naphthyl)-4,4'-diaminobiphenyl (alpha-NPD) was synthesized as follows.

25.1 g (61.5 mmol) of 4,4'-diiodobiphenyl, 2.14 g of poly (ethylene glycol) PEG-6000 that was available from Wako Pure Chemical Industries, Ltd., 17.1 g (0.124 mol) of potassium carbonate and 15.7 g (247 mmol) of powdered copper were added to 32.4 g (148 mmol) of N-phenyl-1-naphthylamine. It was heated at 200 degrees Centigrade. It was determined for tracing by the high-speed liquid chromatography. And it was stirred and refluxed for 12 hours until no peaks of starting materials and intermediates were determined. DMF and water were added thereto to disperse. It was filtrated and washed with water. Precipitated crystals were purified by silica gel column chromatography to obtain 20.2 g of alpha-NPD that is represented by Compound Example 4 at 55.9% yield.

Incidentally, when the similar procedures of Synthetic Example 4 were executed except for using 1.57 g of powdered copper and heating at 250 degrees Centigrade, the same alpha-NPD was obtained.

Synthetic Example 5

N,N'-diphenyl-bis(2-naphthyl)-4,4'-diaminobiphenyl (beta-NPD) was synthesized by the similar procedure of Synthetic Example 4 except for using N-phenyl-2-naphthylamine instead of N-phenyl-1-naphthylamine.

25.1 g (61.5 mmol) of 4,4'-diiodobiphenyl, 2.14 g of poly (ethylene glycol) PEG-6000 that was available from Wako Pure Chemical Industries, Ltd., 17.1 g (0.124 mol) of potassium carbonate and 15.7 g (247 mmol) of powdered copper were added to 32.4 g (148 mmol) of N-phenyl-2-naphthylamine. It was heated at 200 degrees Centigrade. It was determined for tracing by the high-speed liquid chromatography. And it was stirred and refluxed for 12 hours until no peaks of starting materials and intermediates were determined. DMF and water were added thereto to disperse. It was filtrated and washed with water. Precipitated crystals were purified by silica gel column chromatography to obtain 26.2 g of beta-NPD that is represented by Compound Example 5 at 72.4% yield.

Incidentally, when the similar procedures of Synthetic Example 5 were executed except for adding 40 ml of supplemental o-dichlorobenzene and heating to reflux, the same beta-NPD was obtained.

The triarylamine dimer derivatives having the crystal phase synthesized in Synthetic Examples 1 to 5 were identified with the desired derivatives by infrared spectroscopy, $^1$H-nuclear magnetic resonance, $^{13}$C-nuclear magnetic resonance, the elemental analysis and the high-speed liquid chromatography.

The amorphous transformation of the triarylamine dimer derivatives having the crystal phase synthesized in Synthetic Examples 1 to 5 was executed. Examples for preparing the triarylamine dimer derivatives having the amorphous phase of the present invention were explained as following Examples 1 to 6.

Example 1

The amorphous transformation of 3,3-TPD by quenching was executed as follows.

The 3,3-TPD prepared in Synthetic Example 1 was added to a round-bottom flask equipping a mantle heater. It was heated and fused under reduced pressure at 220 degrees Centigrade for 1 hour. The mantle heater was taken off. The flask was ventilated by a drier for about 1 minute, and then quenched by a water bath. The yellow glassy solid was obtained. It was grinded by a mortar. Powder X-ray diffractometry thereof was determined. Having the amorphous phase was confirmed. The spectrum of the determined result is shown in FIG. 1.

Example 2

The amorphous transformation of 4,4-TPD by quenching was executed as follows.

Figure 2:
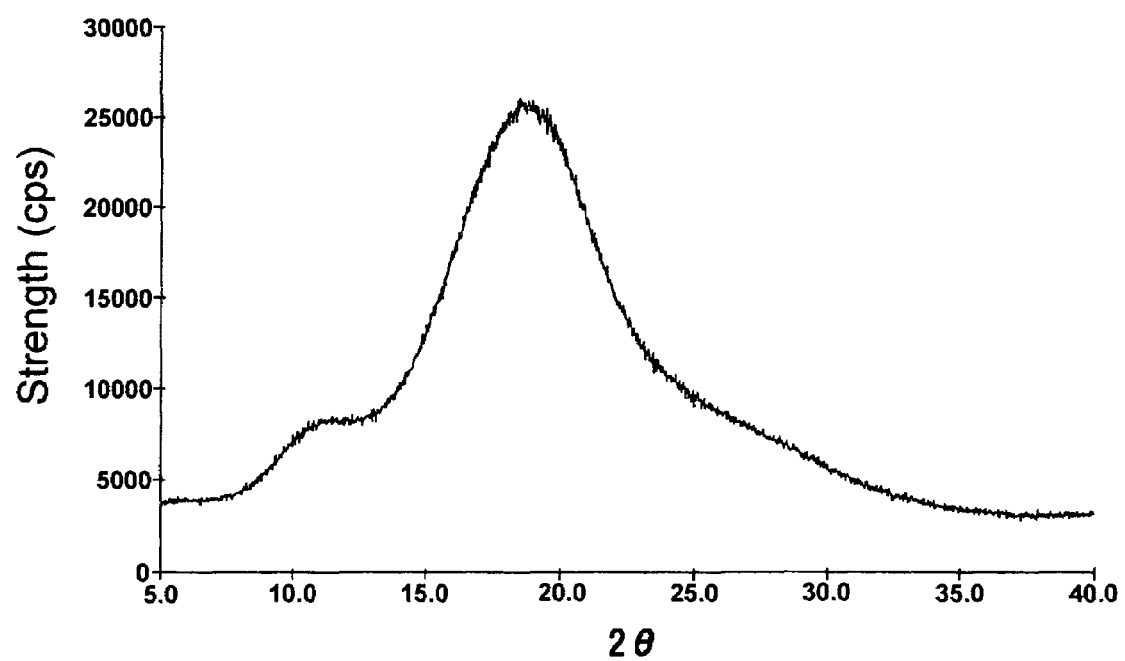
FIG. 2 is a powder X-ray diffractometry spectrum of 4,4-TPD having the amorphous phase prepared in Example 2.

The amorphous 4,4-TPD was obtained by the similar procedure of Example 1 except for using 4,4-TPD synthesized in Synthetic Example 2 and heating at 190 degrees Centigrade The spectrum of the determined result by the similar powder X-ray diffractometry in Example 1 is shown in FIG. 2.

Example 3

The amorphous transformation of mixture of TPD by quenching was executed as follows.

Figure 3:
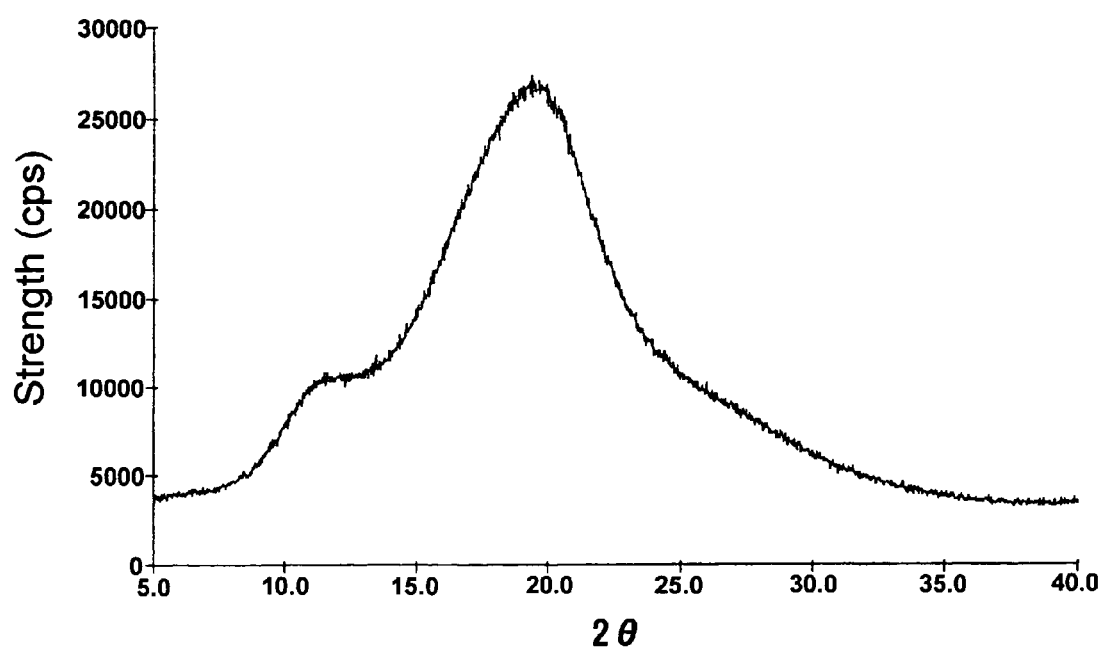
FIG. 3 is a powder X-ray diffractometry spectrum of mixture of TPD having the amorphous phase prepared in Example 3.

The amorphous mixture of TPD was obtained by the similar procedure of Example 1 except for using mixture of TPD synthesized in Synthetic Example 3 and heating at 190 degrees Centigrade. The spectrum of the determined result by the similar powder X-ray diffractometry in Example 1 is shown in FIG. 3.

Example 4

The amorphous transformation of alpha-NPD by quenching was executed as follows.

Figure 4:
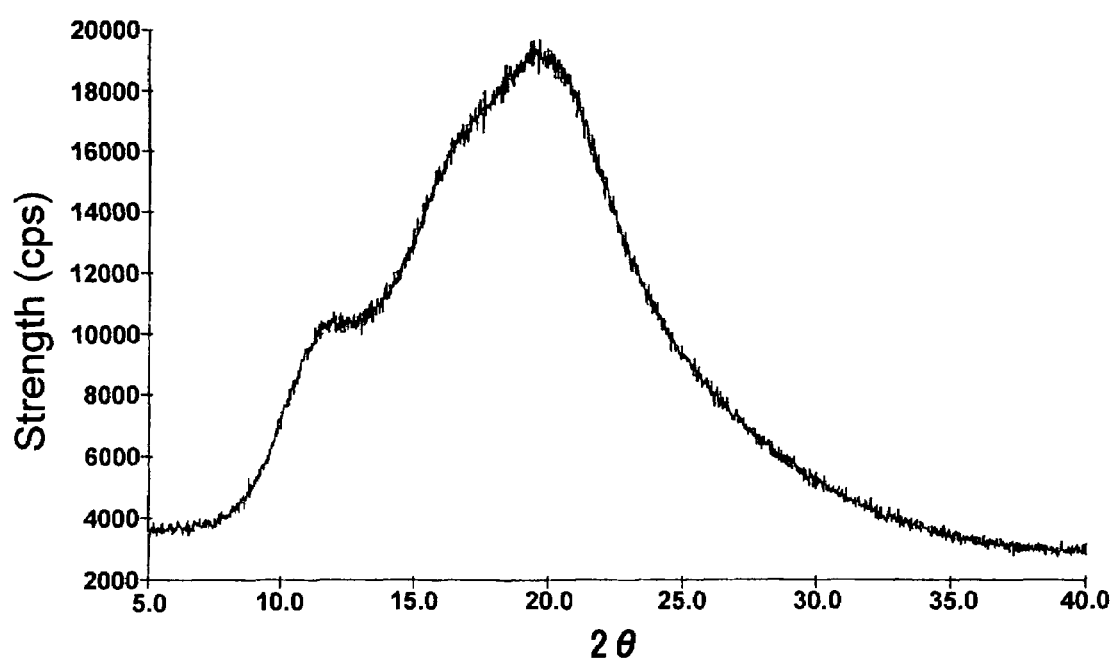
FIG. 4 is a powder X-ray diffractometry spectrum of alpha-NPD having the amorphous phase prepared in Example 4.

The amorphous alpha-NPD was obtained by the similar procedure of Example 1 except for using alpha-NPD synthesized in Synthetic Example 4 and heating at 300 degrees Centigrade for 2 hours. The spectrum of the determined result by the similar powder X-ray diffractometry in Example 1 is shown in FIG. 4.

Example 5

The amorphous transformation of beta-NPD by quenching was executed as follows.

Figure 5:
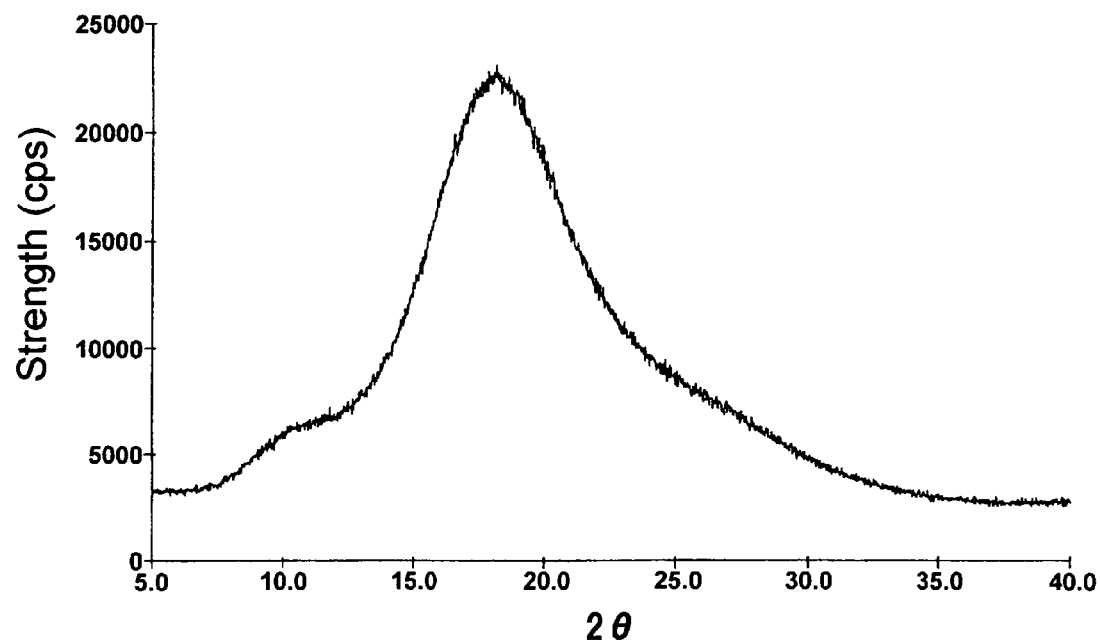
FIG. 5 is a powder X-ray diffractometry spectrum of beta-NPD having the amorphous phase prepared in Examples 5 or 6.

The amorphous beta-NPD as yellow glassy solid was obtained at 84.9% yield by the similar procedure of Example 1 except for using beta-NPD synthesized in Synthetic Example 5 and heating at 175 to 195 degrees Centigrade for 6 hours. The spectrum of the determined result by the similar powder X-ray diffractometry in Example 1 is shown in FIG. 5.

Figure 6:
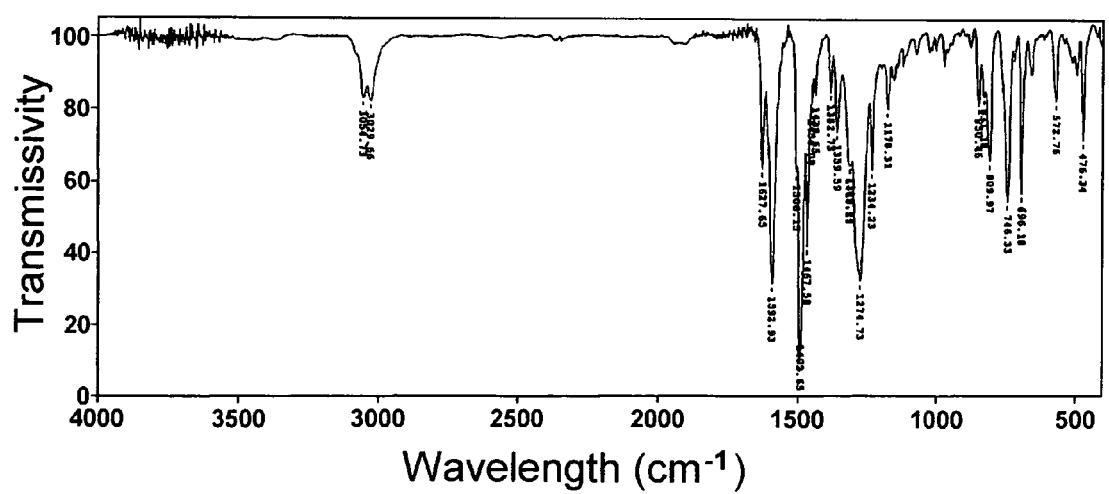
FIG. 6 is an infrared spectroscopy spectrum of beta-NPD prepared in Example 5.
Figure 7:
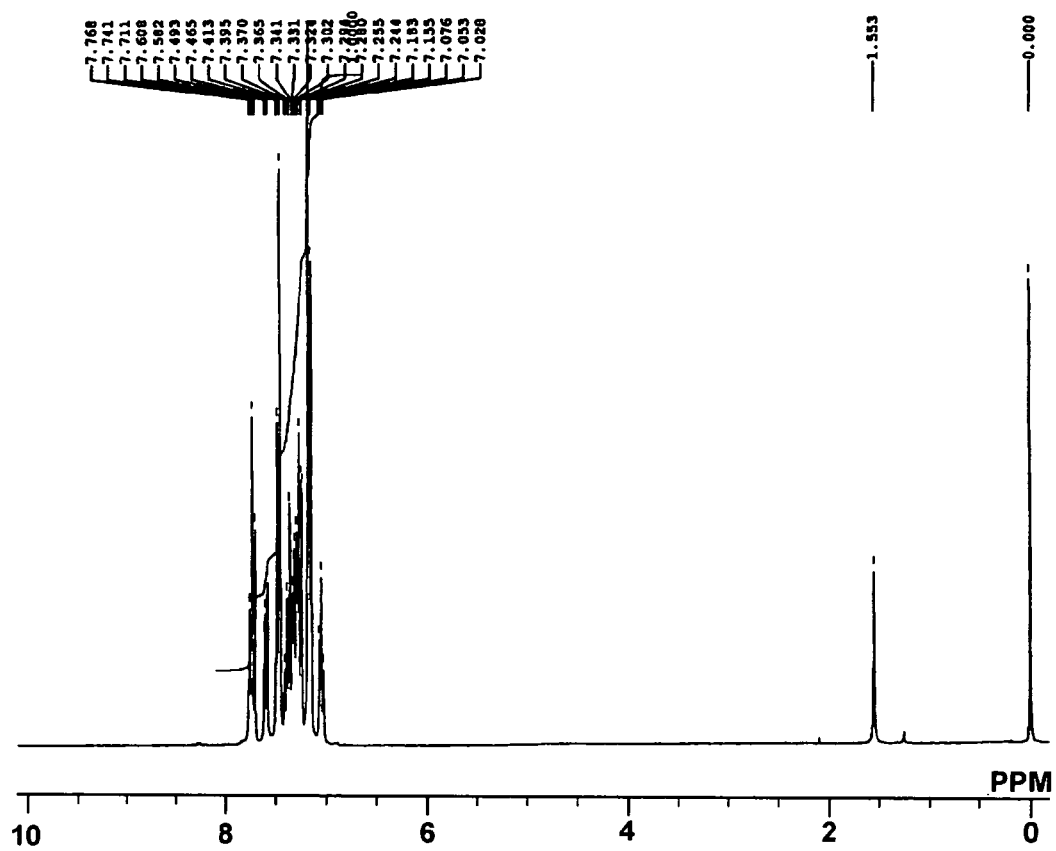
FIG. 7 is a $^1$H-nuclear magnetic resonance spectrum of beta-NPD prepared in Example 5.
Figure 8:
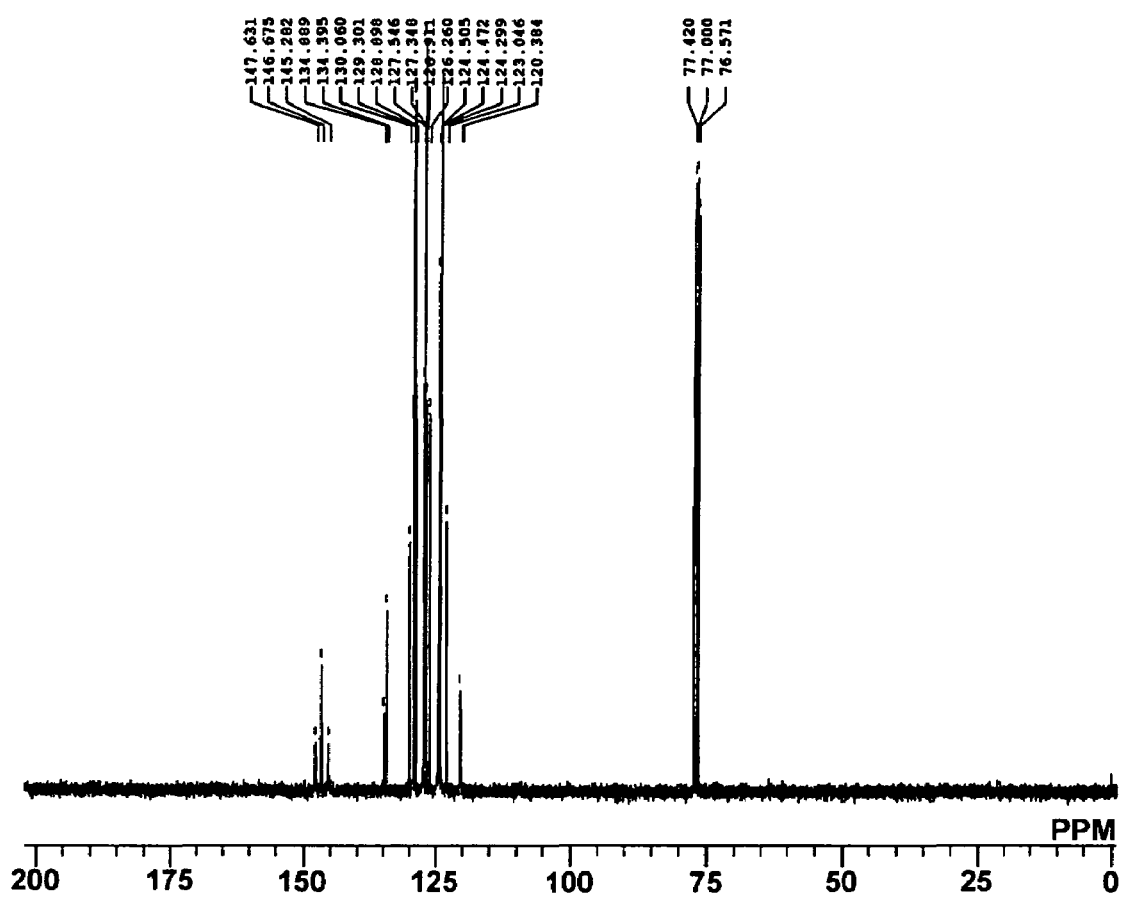
FIG. 8 is a $^{13}$C-nuclear magnetic resonance spectrum of beta-NPD prepared in Example 5.

The result of the elemental analysis of the triarylamine dimer derivative having the amorphous phase beta-NPD prepared in Example 5 is shown in Table 1. The spectrum of the infrared spectroscopy thereof is shown in FIG. 6. The spectrum of the $^1$H-nuclear magnetic resonance thereof is shown in FIG. 7. The spectrum of the $^{13}$C-nuclear magnetic resonance thereof is shown in FIG. 8. The results support the structure of beta-NPD.

TABLE 1

|  | C | H | N |
|---|---|---|---|
| Calculated Value (%) | 89.76 | 5.48 | 4.76 |
| Determined Value (%) | 90.08 | 5.33 | 4.74 |

Example 6

The amorphous transformation of beta-NPD by re-precipitating was executed as follows.

The beta-NPD having amorphous phase was obtained by procedures of dissolving the crystal beta-NPD, which is synthesized in Synthetic Example 5, into the organic solvent, adding the poor solubility solvent thereto and re-precipitating. Concretely, 10 g of the solid synthesized in Synthetic Example 5 was dissolved into 100 ml of DMF under stirring at room temperature. 500 ml of methanol was added thereto. The precipitated solid was filtrated and dried to obtain 9.52 g of the beta-NPD having the amorphous phase. It is confirmed that the obtained amorphous beta-NPD is identified with the amorphous one obtained in Example 5 by the result of powder X-ray diffractometry and the other data.

Comparative Example 1

Figure 9:
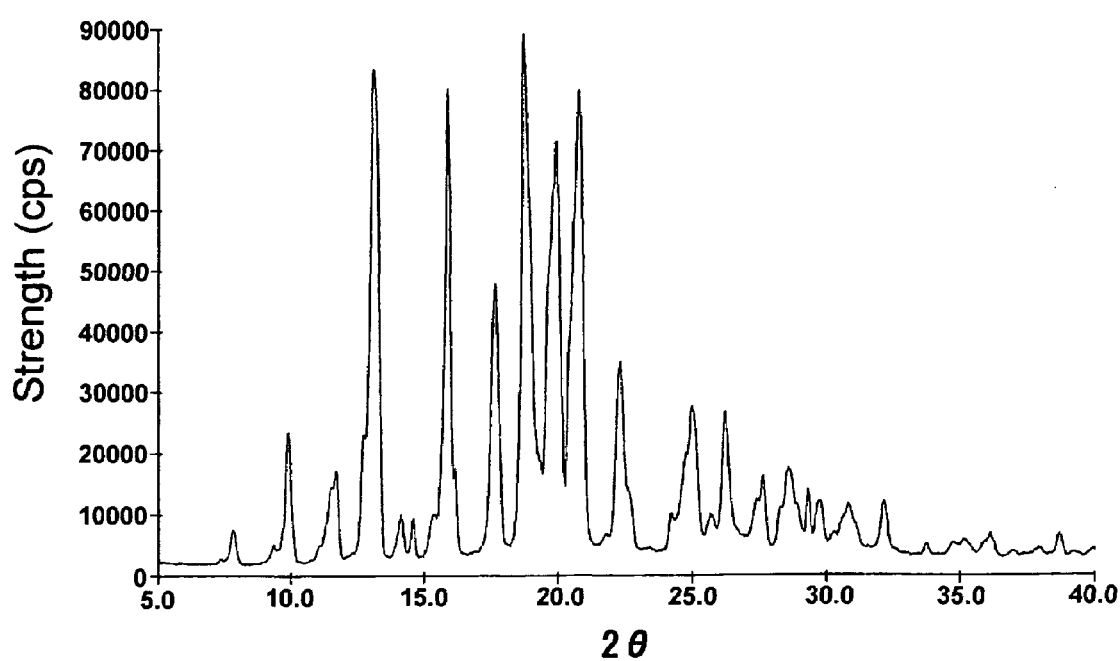
FIG. 9 is a powder X-ray diffractometry spectrum of 3,3-TPD having the crystal phase prepared in Comparative Example 1.

The solid of Comparative Example 1 was 3,3-TPD having the crystal phase synthesized in Synthetic Example 1. The spectrum of the determined result by the similar powder X-ray diffractometry in Example 1 is shown in FIG. 9.

Comparative Example 2

Figure 10:
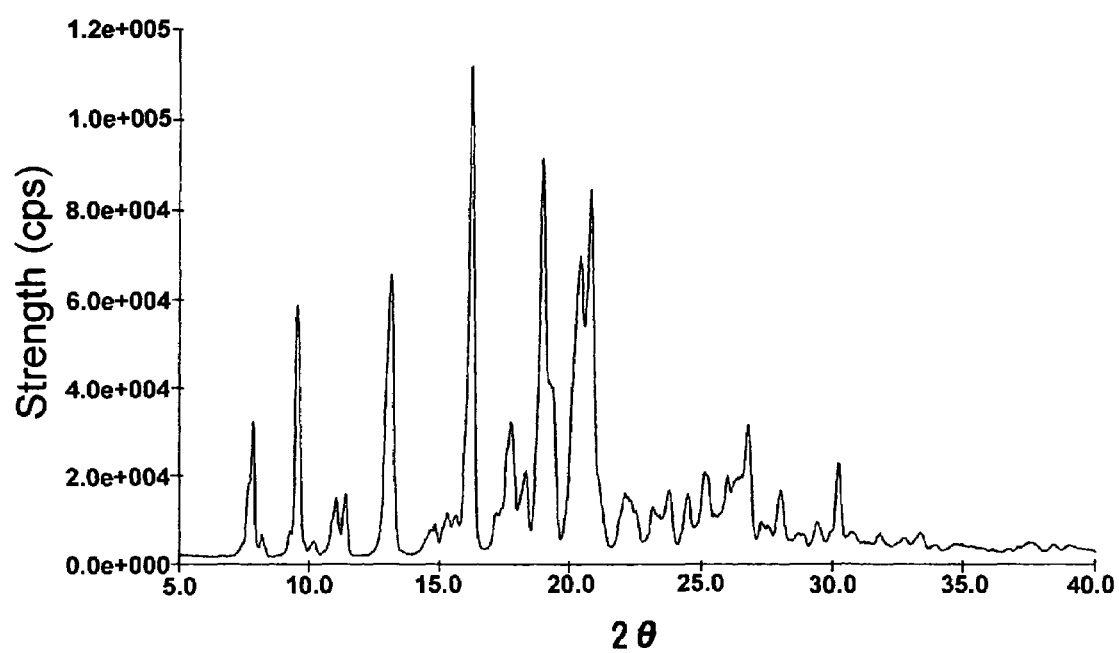
FIG. 10 is a powder X-ray diffractometry spectrum of 4,4-TPD having the crystal phase prepared in Comparative Example 2.

The solid of Comparative Example 2 was 4,4-TPD having the crystal phase synthesized in Synthetic Example 2. The spectrum of the determined result by the similar powder X-ray diffractometry in Example 1 is shown in FIG. 10.

Comparative Example 3

Figure 11:
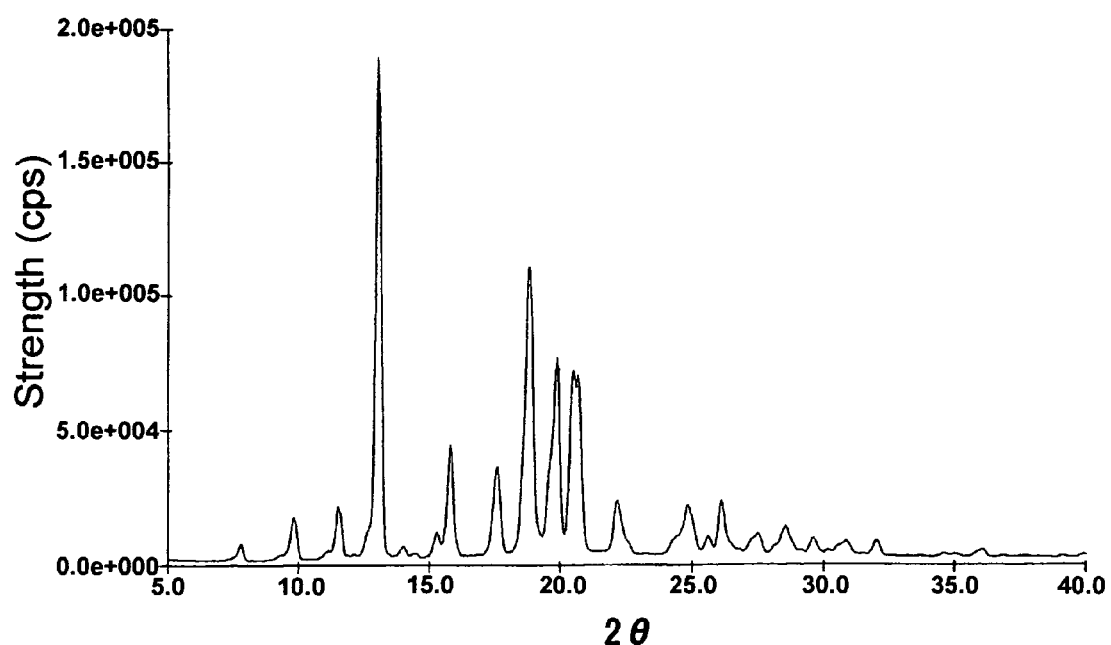
FIG. 11 is a powder X-ray diffractometry spectrum of mixture of TPD having the crystal phase prepared in Comparative Example 3.

The solid of Comparative Example 3 was mixture of TPD having the crystal phase synthesized in Synthetic Example 3. The spectrum of the determined result by the similar powder X-ray diffractometry in Example 1 is shown in FIG. 11.

Comparative Example 4

Figure 12:
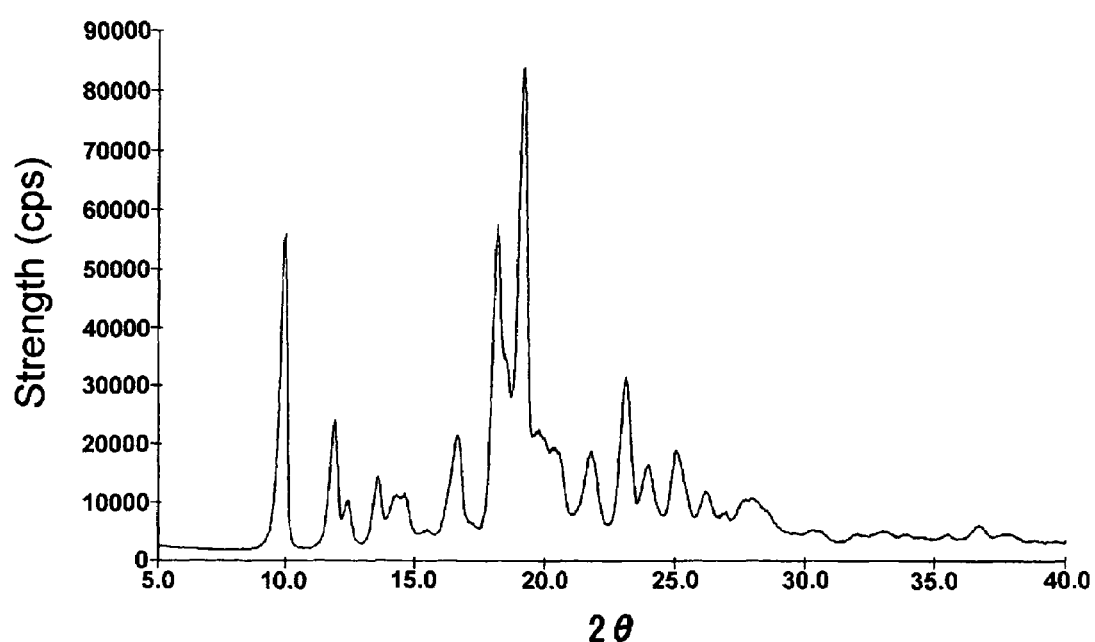
FIG. 12 is a powder X-ray diffractometry spectrum of alpha-NPD having the crystal phase prepared in Comparative Example 4.

The solid of Comparative Example 4 was alpha-NPD having the crystal phase synthesized in Synthetic Example 4. The spectrum of the determined result by the similar powder X-ray diffractometry in Example 1 is shown in FIG. 12.

Comparative Example 5

Figure 13:
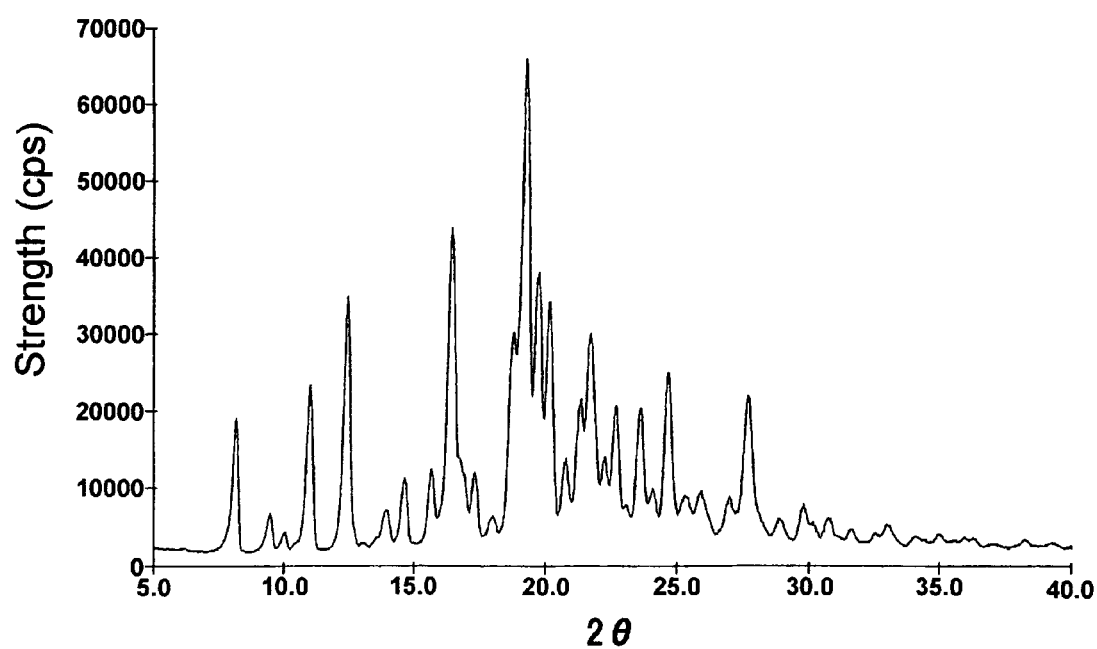
FIG. 13 is a powder X-ray diffractometry spectrum of beta-NPD having the crystal phase prepared in Comparative Example 5.

The solid of Comparative Example 5 was beta-NPD having the crystal phase synthesized in Synthetic Example 5. The spectrum of the determined result by the similar powder X-ray diffractometry in Example 1 is shown in FIG. 13.

Comparative Example 6

Figure 14:
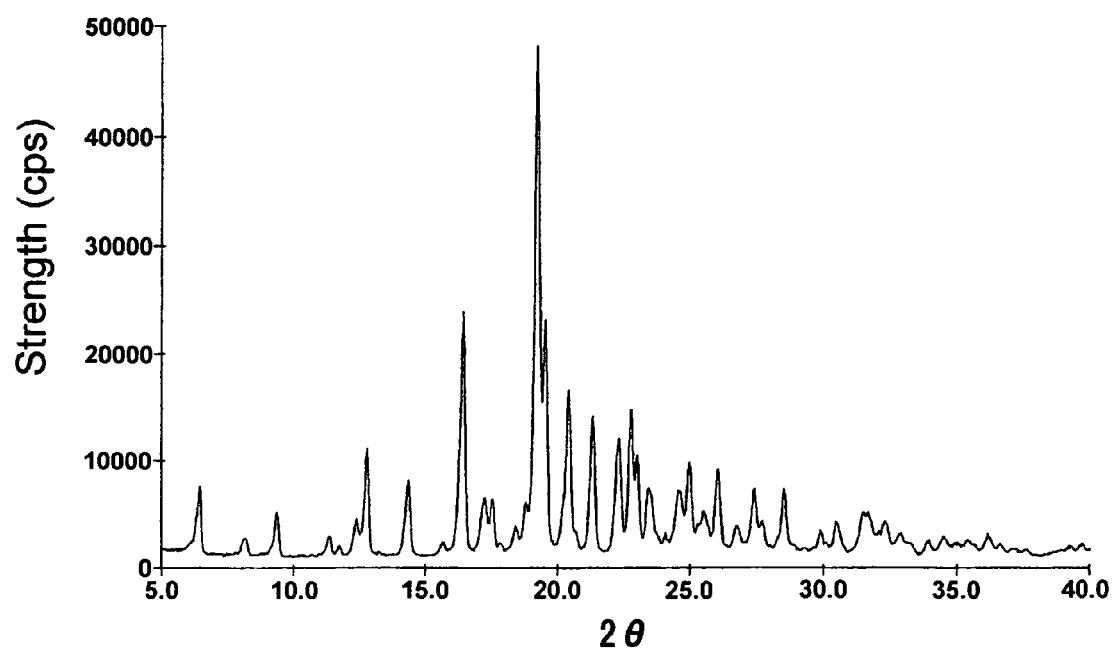
FIG. 14 is a powder X-ray diffractometry spectrum of beta-NPD having the crystal phase prepared in Comparative Example 6.

The Crystal Transformation of Beta-NPD:

The amorphous beta-NPD obtained in Example 5 was re-crystallized using chloroform. It was filtrated and dried to obtain the beta-NPD having the crystal phase. The spectrum of the determined result by the similar powder X-ray diffractometry in Example 1 is shown in FIG. 14.

Comparative Example 7

Figure 15:
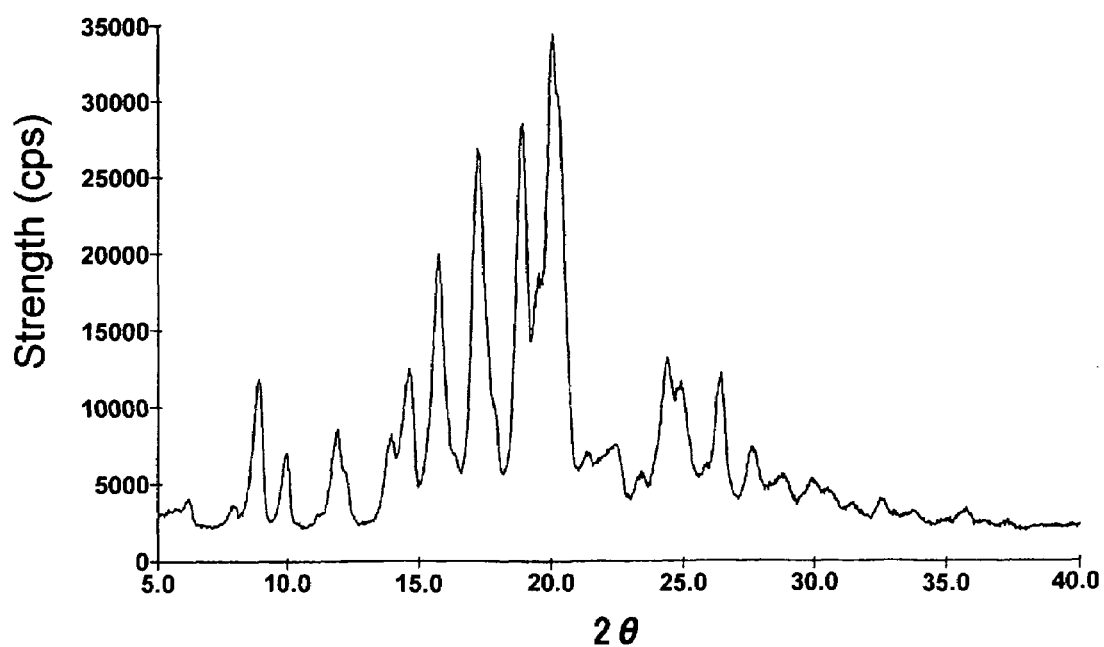
FIG. 15 is a powder X-ray diffractometry spectrum of beta-NPD having the crystal phase prepared in Comparative Example 7.

The Crystal Transformation of Beta-NPD:

The amorphous beta-NPD obtained in Example 5 was dispersed into methanol and stirred at room temperature for 24 hours. It was filtrated and dried to obtain the beta-NPD having the crystal phase. The spectrum of the determined result by the similar powder X-ray diffractometry in Example 1 is shown in FIG. 15.

(Determination of the Solubility)

Respectively, 5 ml of the solvents of THF, DMF, xylene, chloroform and dichloromethane were measured and poured into 20 ml of tubular bottoms with screw caps. They were stirred with magnetic stirrers and added gradually the triarylamine dimer derivative obtained in Examples 1 to 5 and Comparative Examples 1 to 7. The solubility (g/ml) to the respective solvent was determined from the weight of the triarylamine dimer derivative added until saturation. The results of the determined solubility are shown in Table 2.

TABLE 2

| | Triarylamine Dimer Derivative | Phase Transformation | Solubility (g/ml) | | | | |
|---|---|---|---|---|---|---|---|
| | | | THF | DMF | Xylene | Chloroform | Dichloromethane |
| Example1 | 3,3-TPD | Amorphous | 0.294 | 0.019 | 0.082 | 0.467 | 0.265 |
| Example2 | 4,4-TPD | Amorphous | 0.732 | 0.060 | 0.334 | 0.892 | 0.696 |
| Example3 | Mixture of TPD | Amorphous | 0.403 | 0.014 | 0.115 | 0.557 | 0.371 |
| Example4 | alpha-NPD | Amorphous | 0.028 | 0.007 | 0.009 | 0.043 | 0.029 |
| Example5 | beta-NPD | Amorphous | More than 0.795 | 0.301 | 0.558 | 0.632 | 0.471 |
| Example6 | " | " | More than 0.795 | " | " | " | " |
| Comparative Example1 | 3,3-TPD | Crystal | 0.212 | 0.008 | 0.071 | 0.367 | 0.199 |
| Comparative Example2 | 4,4-TPD | Crystal | 0.413 | 0.036 | 0.152 | 0.613 | 0.397 |
| Comparative Example3 | Mixture of TPD | Crystal | 0.319 | 0.012 | 0.106 | 0.491 | 0.302 |
| Comparative Example4 | alpha-NPD | Crystal | 0.009 | 0.001 | 0.002 | 0.024 | 0.021 |
| Comparative Example5 | beta-NPD | Crystal | 0.235 | 0.012 | 0.103 | 0.395 | 0.195 |
| Comparative Example6 | beta-NPD | Crystal | 0.270 | 0.033 | 0.162 | 0.452 | 0.226 |
| Comparative Example7 | beta-NPD | Crystal | 0.202 | 0.028 | 0.155 | 0.368 | 0.209 |

As shown in Table 2, the respective triarylamine dimer derivatives having the amorphous phase such as Examples 1 to 6 had higher solubility than the triarylamine dimer derivatives having the crystal phase such as Comparative Examples 1 to 7 with regard to the corresponding triarylamine dimer derivative. Beta-NPD and 4,4-TPD were remarkable.

Especially, it turned out that beta-NPD having the amorphous phase of Example 5 had very high solubility as compared with 3,3-TPD having the amorphous phase of Example 1 and alpha-NPD having the amorphous phase of Example 4 among the derivatives having the amorphous phase. Moreover it turned out that beta-NPD having the amorphous phase had ten to several hundreds times higher solubility than alpha-NPD that was its isomer.

It is assumed that the solution saturated by the triarylamine dimer derivative having the amorphous phase was in the supersaturation condition because of obvious observation that the crystalline began to precipitate under standing for a long period.

The interaction between the amine molecules having the amorphous phase is weak. Therefore the amine molecules are easily separable in the organic solvent. It is assumed that the supersaturation condition is maintained for a long period, though it exceeds usual solubility.

(Differential Scanning Calorimetry (DSC))

The results of the glass transition point (Tg) determined by DSC of the triarylamine dimer derivatives obtained in Examples 1 to 6 are shown in Table 3.

(Melting Point)

The results of the determined melting point of the triarylamine dimer derivatives having the crystal phase obtained in Comparative Examples 1 to 7 are shown in Table 3.

TABLE 3

| | Triarylamine Dimer Derivative | Phase Transformation | Glass Transition Point(Tg) (Degrees C.) | Melting Point (Degrees C.) |
|---|---|---|---|---|
| Example1 | 3,3-TPD | Amorphous | 63.2 | — |
| Example2 | 4,4-TPD | Amorphous | 75.0 | — |
| Example3 | Mixture of TPD | Amorphous | 68.0 | — |
| Example4 | alpha-NPD | Amorphous | 98.8 | — |
| Example5 | beta-NPD | Amorphous | 99.4 | — |
| Example6 | beta-NPD | Amorphous | 99.4 | — |
| Comparative Example1 | 3,3-TPD | Crystal | — | 170.6 |
| Comparative Example2 | 4,4-TPD | Crystal | — | 166.9 |
| Comparative Example3 | Mixture of TPD | Crystal | — | 163.8 |
| Comparative Example4 | alpha-NPD | Crystal | — | 276.5 |
| Comparative Example5 | beta-NPD | Crystal | — | 147.2 |
| Comparative Example6 | beta-NPD | Crystal | — | — |
| Comparative Example7 | beta-NPD | Crystal | — | 173.0 |

Examples A to D and Comparative Examples A to C are embodiments of manufacturing of the layer-built photosensitive conductor pieces using the compounds obtained in Examples 1, 4, 5, 6, and Comparative Examples 1, 4, 5, respectively.

Example A

The layer-built photosensitive conductor piece using beta-NPD having the amorphous phase was manufactured as follows.

0.2 g of Y-type titanyl phthalocyanine that is prepared by the same procedure of Japanese Patent Provisional Publication No. 3-35064, 0.2 g of polyvinyl butyral resin S-LEC BH-3 that was available from Sekisui Chemical Co., Ltd., 59.6 g of cyclohexanone and 50 g of glass beads having diameter of 3 mm were added to 100 ml flat-bottom bottle. It was shaken by a paint shaker for 1 hour. It was coated by a bar coater onto an aluminum plate washed with acetone finely to form the charge generation layer having thickness of 0.5 microns. 1.0 g of N,N'-diphenyl-N,N'-bis(2-naphthyl)-4,4'-diaminobiphenyl (beta-NPD) that was prepared in Example 5 and 1.0 g of polycarbonate panliteL-1250 that was available from Teijin Limited were dissolved into 11.3 g of dichloromethane. The solution was coated by a bar coater onto the charge generation layer to form the charge transport layer having thickness of 20 microns. And layer-built photosensitive conductor piece was manufactured.

Example B

The layer-built photosensitive conductor piece using beta-NPD having the amorphous phase was manufactured as follows.

The layer-built photosensitive conductor piece was manufactured by the similar procedure of Example A except for using beta-NPD having the amorphous phase prepared in Example 6 instead of using beta-NPD having the amorphous phase prepared in Example 5.

Example C

The layer-built photosensitive conductor piece using 3,3-TPD having the amorphous phase was manufactured as follows.

The layer-built photosensitive conductor piece was manufactured by the similar procedure of Example A except for using 3,3-TPD having the amorphous phase prepared in Example 1 instead of using beta-NPD having the amorphous phase prepared in Example 5.

Example D

The layer-built photosensitive conductor piece using alpha-NPD having the amorphous phase was manufactured as follows.

The layer-built photosensitive conductor piece was manufactured by the similar procedure of Example A except for using alpha-NPD having the amorphous phase prepared in Example 4 instead of using beta-NPD having the amorphous phase prepared in Example 5.

Comparative Example A

The layer-built photosensitive conductor piece using beta-NPD having the crystal phase was manufactured as follows.

The layer-built photosensitive conductor piece was manufactured by the similar procedure of Example A except for using beta-NPD having the crystal phase prepared in Comparative Example 5 instead of using beta-NPD having the amorphous phase prepared in Example 5.

Comparative Example B

The layer-built photosensitive conductor piece using 3,3-TPD having the crystal phase was manufactured as follows.

The layer-built photosensitive conductor piece was manufactured by the similar procedure of Example A except for using 3,3-TPD having the crystal phase prepared in Comparative Example 1 instead of using beta-NPD having the amorphous phase prepared in Example 5.

Comparative Example C

The layer-built photosensitive conductor piece using alpha-NPD having the crystal phase was manufactured as follows.

The layer-built photosensitive conductor piece was manufactured by the similar procedure of Example A except for using alpha-NPD having the crystal phase prepared in Comparative Example 4 instead of using beta-NPD having the amorphous phase prepared in Example 5.

(Evaluation of the Properties of the Photosensitive Conductor)

The properties of the primary photosensitivity (OPC property) of the photosensitive conductor pieces manufactured in the above-mentioned. Examples A to D and Comparative Examples A to C for the evaluation were determined. Electrostatic Paper Analyzer EPA-8200 that is available from Kawaguchi Electric Works Co., Ltd. was used for the determination. It was electrified at −8.0 kV under STAT3 mode thereof, stood for 2.0 seconds in the dark, and then irradiated by 5.0 Lx. of white light for 10.0 seconds.

The electrification potential (Vmax), the dark decrement (%), the residual potential (Vre), the amount of exposure of half-value period that means sensitivity (E½) were determined and evaluated. The results of the above-mentioned determination were summarized in Table 4.

TABLE 4

| | Charge Transport Material | | Electrification | Dark | Residual | Amount of Exposure of Half-value |
|---|---|---|---|---|---|---|
| | Derivative | Phase Transformation | Potential Vmax(V) | Decrement (%) | Potential Vre(V) | Period E½(Lx · s) |
| ExampleA | beta-NPD | Amorphous | −527 | 12.5 | 0.7 | 0.62 |
| ExampleB | beta-NPD | Amorphous | −532 | 11.8 | 0.5 | 0.61 |
| ExampleC | 3 3-TPD | Amorphous | −521 | 16.2 | 0.4 | 0.63 |
| ExampleD | alpha-NPD | Amorphous | — | — | — | — |
| Comparative ExampleA | beta-NPD | Crystal | — | — | — | — |
| Comparative ExampleB | 3 3-TPD | Crystal | −533 | 14.8 | −0.3 | 0.61 |
| Comparative ExampleC | alpha-NPD | Crystal | — | — | — | — |

Incidentally, the dark decrement (%) was calculated by the following equation using the determined surface potential after electrification immediately (V0=Vmax) and the determined surface potential after standing for 2.0 seconds.

the dark decrement (%)=100($V0-V2$)/$V0$

As shown the results of the primary photosensitivity in Table 4, the each results of the electrification potential (Vmax) and the amount of exposure of half-value period are equal approximately although the charge transport materials are different. The results of the dark decrement are excellent, and beta-NPD having the amorphous phase of Example B have the lowest value among them. It is assumed that the charge transport layer was homogeneous excellently.

Especially when the change of the coated layer of the sensitive conductor of Example A that beta-NPD having the amorphous phase was used for the evaluation under the passage of time, was observed by a microscope, the precipitation of crystal was not seen at all after several days. Therefore it is suggested that beta-NPD having the amorphous phase was useful for the charge transport layer and excellently uniform, and had excellent stability especially.

In the other hand, beta-NPD having the crystal phase of Comparative Example A and alpha-NPD having the crystal phase of Comparative Example C had low solubility. Therefore by using them, the coating solution for the charge transport material having sufficient concentration could not be obtained and the photosensitive conductor for the evaluation could not be manufactured.

As explained to the detail above, the triarylamine dimer derivatives having the amorphous phase of the present invention have very sufficient solubility into the organic solvent and the excellent stability thereof. It is used for the forming the charge transport layer of the electrophotographic photosensitive conductor. The electrophotographic photosensitive conductor is manufactured by the simple coating method such as the dipping method or the spin-coating method.

The triarylamine dimer derivative having amorphous phase of the present invention is useful to the charge transport layer and excellently uniform and excellent stability. The organic photosensitive conductor having excellent stability is manufactured using it. Therefore the organic photosensitive conductor has the excellent photosensitive properties such as the electrification potential (Vmax), the amount of exposure of half-value period that means sensitivity (E½), and especially the excellent dark decrement.

What is claimed is:

1. An electrophotographic photosensitive conductor having a charge transport material that includes a triarylamine dimer derivative represented by the following chemical formula [3] or [4]

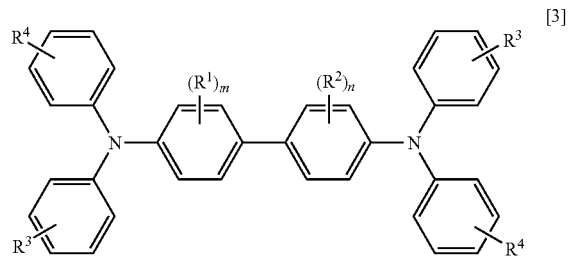

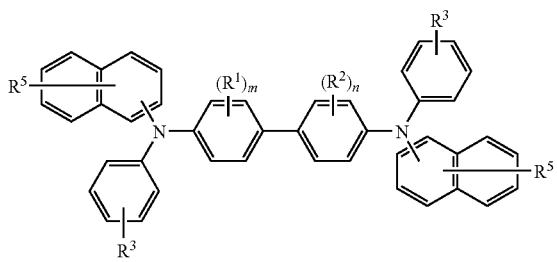

wherein —$R^1$ and —$R^2$ are same or different and are selected from the group consisting of a hydrogen atom, an alkyl group having 1 to 4 carbons, an alkoxyl group having 1 to 4 carbons, and a halogen atom, —$R^3$, —$R^4$ and —$R^5$ are same or different and are selected from the group consisting of a hydrogen atom, an alkyl group having 1 to 4 carbons, an alkoxyl group having 1 to 4 carbons, a vinyl group, a propenyl group, a butenyl group, an ethynyl group, a propargyl group, a dimethylamino group, a diethylamino group, an imino group, and a halogen atom, m and n are from 0 to 4;

wherein the triarylamine dimer derivative is in an amorphous phase.

2. The electrophotographic photosensitive conductor according to claim 1, wherein the derivative is N,N'-diphenyl-N,N'-bis(2-naphthyl)-4,4'-diaminobiphenyl represented by the following chemical formula [2]

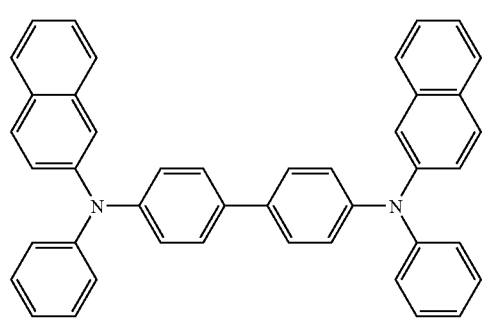

3. The electrophotographic photosensitive conductor according to claim 1, wherein the derivative is manufactured by an amorphous manufacturing method, comprising:
providing a a solid of the derivative represented by the chemical formula [3] or [4] in a crystal phase,
heating and fusing same,
then quenching and solidifying same, thereby obtaining the derivative represented by the chemical formula [3] or [4] in an amorphous phase.

4. The electrophotographic photosensitive conductor according to claim 1, wherein the derivative is manufactured by an amorphous manufacturing method, comprising:
providing a a solid of the derivative represented by the chemical formula [3] or [4] in a crystal phase,
dissolving same into an organic solvent,
then re-precipitating same by addition of a solvent in which the derivative is poorly soluble, thereby obtaining the derivative represented by the chemical formula [3] or [4] in an amorphous phase.

5. The electrophotographic photosensitive conductor according to claim 3, wherein the quenching is conducted at a temperature in the range from a fusing temperature of the triarylamine dimer derivative to its glass transition point or below.

6. The electrophotographic photosensitive conductor according to claim 4, wherein the organic solvent is selected from the group consisting of xylene, dichloromethane, chloroform, tetrahydrofuran, dimethyl formamide and ethyl acetate; and the solvent in which the derivative is poorly soluble is an alcohol solvent selected from the group consisting of methanol, ethanol, isopropanol and butanol.

* * * * *